(12) United States Patent
Utamura

(10) Patent No.: US 10,737,993 B2
(45) Date of Patent: Aug. 11, 2020

(54) METHOD FOR PRODUCING INDANCARBALDEHYDE

(71) Applicant: MITSUBISHI GAS CHEMICAL COMPANY, INC., Chiyoda-ku (JP)

(72) Inventor: Tatsuya Utamura, Kurashiki (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 0 days.

(21) Appl. No.: 16/605,628

(22) PCT Filed: Mar. 9, 2018

(86) PCT No.: PCT/JP2018/009136
§ 371 (c)(1),
(2) Date: Oct. 16, 2019

(87) PCT Pub. No.: WO2018/193749
PCT Pub. Date: Oct. 25, 2018

(65) Prior Publication Data
US 2020/0140360 A1    May 7, 2020

(30) Foreign Application Priority Data
Apr. 18, 2017    (JP) .................. 2017-082178

(51) Int. Cl.
*C07C 45/49* (2006.01)
*C07C 47/546* (2006.01)

(52) U.S. Cl.
CPC ............ *C07C 45/49* (2013.01); *C07C 47/546* (2013.01)

(58) Field of Classification Search
CPC .................................................. C07C 45/49
USPC ......................................................... 568/428
See application file for complete search history.

(56) References Cited

U.S. PATENT DOCUMENTS

| 2,485,237 A | 10/1949 | Gresham et al. |
| 3,962,343 A | 6/1976 | Fujiyama et al. |
| 3,968,163 A | 7/1976 | Solomons et al. |
| 3,988,424 A | 10/1976 | Fujiyama et al. |
| 4,460,794 A * | 7/1984 | Fujiyama ................ C07C 45/49 568/428 |
| 4,622,429 A | 11/1986 | Blank et al. |

FOREIGN PATENT DOCUMENTS

| JP | 39-29760 | 12/1964 |
| JP | 53-14059 | 5/1978 |
| JP | 1-165532 A | 6/1989 |
| JP | 7-96505 B2 | 6/1989 |
| JP | 9-301898 A | 11/1997 |

OTHER PUBLICATIONS

Francio, G. et al., "Highly efficient enantioselective catalysis in supercritical carbon dioxide using the perfluoroalkyl-substituted ligand (R,S)-3-$H^2$-$F^6$-BINAPHOS," Journal of Organometallic Chemistry, vol. 621, 2001, pp. 130-142.

* cited by examiner

*Primary Examiner* — Yong L Chu
(74) *Attorney, Agent, or Firm* — Oblon, McClelland, Maier & Neustadt, L.L.P.

(57) ABSTRACT

The present invention provides a method for producing indancarbaldehyde, including a step of reacting indan with carbon monoxide in the presence of hydrogen fluoride and boron trifluoride to obtain a reaction liquid including indancarbaldehyde, wherein
the indan includes an amine, and a content of the amine is less than 1000 ppm by mass.

12 Claims, No Drawings

METHOD FOR PRODUCING INDANCARBALDEHYDE

TECHNICAL FIELD

The present invention relates to a method for producing indancarbaldehyde useful as a raw material for the production of various industrial chemical raw materials, perfumes, medicines, agricultural chemicals, optical functional materials, electronic functional materials, and the like.

BACKGROUND ART

A reaction in which an alkylbenzene and carbon monoxide are reacted using hydrogen chloride-aluminum chloride or the like as a catalyst to produce an alkylbenzaldehyde is known as the Gattermann-Koch reaction. In this production, in order to separate the product and the catalyst after the completion of the reaction, usually, the reaction mixture is treated with water, and therefore the regeneration of the catalyst is very difficult. In addition, also when the catalyst used in the reaction is discarded, hydrolysis treatment is required, and therefore a problem is that a large amount of waste is generated, and the treatment cost increases.

As one of the types of the Gattermann-Koch reaction, a method of using hydrogen fluoride and boron trifluoride as catalysts is disclosed (see Patent Literature 1 and Patent Literature 2). In this type, substances having high vapor pressure, hydrogen fluoride and boron trifluoride, are used as catalysts, and therefore hydrolysis is not required for the separation of the product and the catalysts, and hydrogen fluoride and boron trifluoride can be circulated and reused, and this type is one of industrially very excellent aromatic aldehyde production methods. As a method for recovering hydrogen fluoride and boron trifluoride from an alkylbenzaldehyde-hydrogen fluoride-boron trifluoride complex solution that is a product of the Gattermann-Koch reaction in which hydrogen fluoride and boron trifluoride are used as catalysts, specifically, a method of thermally decomposing the complex solution under pressurization using benzene as a heat medium is disclosed (see Patent Literature 3).

Indene is one of aromatic compounds and is a compound useful as a raw material of various industrial chemical materials, perfumes, medicines, agricultural chemicals, optical functional materials, electronic functional materials, and the like.

Indene is generally obtained by distillation from coal tar fractions, and contains benzonitrile, phenols, pyridines, anilines, and the like as impurities. These impurities contained in indene cause side reactions in a reaction system and/or in the subsequent purification step and the like and cause a decrease in productivity and therefore are desirably removed. Among the above impurities, phenols, pyridines, and anilines can be removed by treatment with an alkali or an acid. On the other hand, benzonitrile is neutral, cannot be removed even by treatment with an acid or an alkali, and is difficult to completely separate even by precision distillation.

As a method for removing benzonitrile from indene, Patent Literature 4 discloses a method in which a solid alkali is added to tar-based light oil containing indene, the mixture is heat-treated at a temperature of 100° C. or more, and the precipitated insoluble matter is removed followed by distillation to recover indene.

In addition, Patent Literature 5 discloses a method in which a coal tar fraction comprising indene is catalytically reduced to obtain a mixture in which indene is converted into indan, and benzonitrile contained as an impurity is converted into amines such as benzylamine, dibenzylamine, and tribenzylamine, and this mixture is acid-washed to remove the amines contained in the mixture.

CITATION LIST

Patent Literature

Patent Literature 1: U.S. Pat. No. 2,485,237
Patent Literature 2: Japanese Examined Patent Application Publication No. 39-29760
Patent Literature 3: Japanese Examined Patent Application Publication No. 53-14059
Patent Literature 4: Japanese Unexamined Patent Application Publication No. 9-301898
Patent Literature 5: Japanese Unexamined Patent Application Publication No. 7-96505

SUMMARY OF INVENTION

Technical Problem

When indan is obtained by the catalytic reduction of indene under a hydrogen atmosphere, some or the total amount of benzonitrile contained in indene is simultaneously reduced to produce amines comprising benzylamine, dibenzylamine, and tribenzylamine. The boiling point of benzylamine is 183° C. at normal pressure and close to the boiling point of indan, 177° C. at normal pressure, and it is not easy to completely separate benzylamine and indan by precision distillation.

When indancarbaldehyde is produced by the Gattermann-Koch reaction using indan containing the above amines, and hydrogen fluoride and boron trifluoride as catalysts, the amines form strong complexes with boron trifluoride. Boron trifluoride forms stable complexes with ethers and/or amines. Particularly, complexes of boron trifluoride and amines are solids stable at normal temperature and pressure, and, for example, a boron trifluoride-benzylamine complex is a compound solid at normal temperature and pressure having a melting point of 137° C. and a boiling point of 185° C.

Therefore, when the method of thermally decomposing an alkylbenzaldehyde-hydrogen fluoride-boron trifluoride complex described in Patent Literature 3 is applied to the production of indancarbaldehyde from indan by the Gattermann-Koch reaction described above, conditions of a higher temperature and pressure than conventional ones are required, and it is necessary to provide equipment having a reactor material and/or structure that can withstand the conditions, thereby causing an increase in production cost. In addition, a problem of the undecomposed benzylamine-boron trifluoride complex is that it promotes the degradation of indancarbaldehyde under the thermal decomposition conditions. A further problem of the undecomposed benzylamine-boron trifluoride complex is that solids precipitate in the production equipment to cause a decrease in the productivity of indancarbaldehyde.

For an aldehyde that is a product of the Gattermann-Koch reaction, the aldehyde, hydrogen fluoride, and boron trifluoride form a complex as described above. Therefore, also in the production of indancarbaldehyde by the Gattermann-Koch reaction, it is required to recover indancarbaldehyde, which is the target substance, hydrogen fluoride, and boron trifluoride in good yield from the indancarbaldehyde-hydrogen fluoride-boron trifluoride complex solution after the reaction to improve the productivity of indancarbaldehyde. The recovered hydrogen fluoride and boron trifluoride can be used again in the reaction as catalysts, and therefore the improvement of the recovery rates is desired from the viewpoint of reducing the production cost.

When the alkali treatment method described in Patent Literature 4 is applied to decrease benzonitrile, which is a cause of the production of amines, the treatment of generated wastewater and insoluble matter is required. In addition, also when the method described in Patent Literature 5 is applied to remove amines produced from benzonitrile, the treatment of wastewater comprising the amines is required, and the number of steps required increases, and therefore the method is not an industrially advantageous method for producing indancarbaldehyde.

It is an object of the present invention to provide an industrially advantageous method for producing indancarbaldehyde in which in the production of indancarbaldehyde by the Gattermann-Koch reaction using hydrogen fluoride and boron trifluoride as catalysts, the degradation of indancarbaldehyde due to a benzylamine-boron trifluoride complex is suppressed, and indancarbaldehyde, hydrogen fluoride, and boron trifluoride can be recovered in good yield from an indancarbaldehyde-hydrogen fluoride-boron trifluoride complex solution that is the reaction product.

Solution to Problem

The present inventor has diligently studied a method for producing indancarbaldehyde, and as a result found that by reacting indan having a content of an amine of less than 1000 ppm by mass with carbon monoxide in the presence of hydrogen fluoride and boron trifluoride, the production of a benzylamine-boron trifluoride complex is suppressed, the degradation of indancarbaldehyde can be suppressed, indancarbaldehyde, hydrogen fluoride, and boron trifluoride can be recovered in good yield from an indancarbaldehyde-hydrogen fluoride-boron trifluoride complex solution, and indancarbaldehyde can be industrially advantageously produced. Thus, the present inventor has completed the present invention.

Specifically, the present invention is as follows.

[1]

A method for producing indancarbaldehyde, comprising a step of reacting indan with carbon monoxide in the presence of hydrogen fluoride and boron trifluoride to obtain a reaction liquid comprising indancarbaldehyde, wherein the indan comprises an amine, and a content of the amine is less than 1000 ppm by mass.

[2]

The method for producing indancarbaldehyde according to [1], wherein the indan is a reaction product of a hydrogenation reaction of a raw material comprising indene.

[3]

The method for producing indancarbaldehyde according to [2], wherein a content of the indene contained in the raw material is 90% by mass or more.

[4]

The method for producing indancarbaldehyde according to [2] or [3], wherein the raw material comprising the indene comprises benzonitrile, and a content of the benzonitrile is 0.5 to 10% by mass.

[5]

The method for producing indancarbaldehyde according to any of [1] to [4], wherein the indan comprises benzonitrile, and a content of the benzonitrile is 0.5 to 10% by mass.

[6]

The method for producing indancarbaldehyde according to any of [1] to [5], wherein the indancarbaldehyde is indan-5-carbaldehyde represented by formula (1).

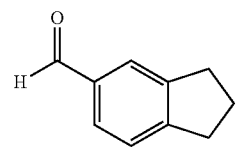

(1)

[7]

The method for producing indancarbaldehyde according to any of [1] to [6], wherein the amine contained in the indan is one or more selected from the group consisting of benzylamine, dibenzylamine, and tribenzylamine.

[8]

The method for producing indancarbaldehyde according to any of [1] to [7], further comprising a step of adding a heat medium to the reaction liquid comprising the indancarbaldehyde followed by heating for separation into a flow comprising the hydrogen fluoride and the boron trifluoride and a flow comprising the indancarbaldehyde and the heat medium.

[9]

The method for producing indancarbaldehyde according to [8], wherein the heating is performed under conditions of a temperature of 120 to 180° C. and 0.1 to 1.0 MPa in terms of gauge pressure.

[10]

The method for producing indancarbaldehyde according to any of [1] to [9], further comprising steps of: reducing a raw material comprising indene in the presence of a catalyst and hydrogen to obtain a reaction product comprising indan, and distilling and purifying the reaction product comprising the indan to obtain indan having a content of an amine of less than 1000 ppm by mass.

[11]

The method for producing indancarbaldehyde according to [10], wherein the reduction is performed under conditions of a temperature of 20 to 100° C. and normal pressure to 2.0 MPa in terms of gauge pressure.

[12]

The method for producing indancarbaldehyde according to [10] or [11], wherein the catalyst comprises a catalyst comprising palladium and/or platinum.

Advantageous Effects of Invention

In the production method of the present invention, the degradation of indancarbaldehyde due to a benzylamine-boron trifluoride complex is suppressed, indancarbaldehyde, hydrogen fluoride, and boron trifluoride can be recovered in good yield from an indancarbaldehyde-hydrogen fluoride-boron trifluoride complex solution that is the reaction product, and indancarbaldehyde can be industrially advantageously produced.

The present invention allows producing indancarbaldehyde useful as a raw material for the production of various industrial chemical raw materials, perfumes, medicines, agricultural chemicals, optical functional materials, and electronic functional materials, by an industrially advantageous method.

DESCRIPTION OF EMBODIMENT

A mode for carrying out the present invention (hereinafter referred to as "this embodiment") will be described in detail below. The present invention is not limited to this embodiment below, and various modifications can be made without departing from the spirit thereof.

The production method in this embodiment is a method for producing indancarbaldehyde, comprising a step of reacting indan with carbon monoxide in the presence of hydrogen fluoride and boron trifluoride to obtain a reaction liquid comprising indancarbaldehyde, wherein
the indan comprises an amine, and the content of the amine is less than 1000 ppm by mass. The content of the amine is preferably less than 900 ppm by mass, more preferably less than 800 ppm by mass, further preferably less than 700 ppm by mass, still further preferably less than 650 ppm by mass, and still more preferably less than 150 ppm by mass.

When the content of the amine is less than 1000 ppm by mass, the production of a benzylamine-boron trifluoride complex is suppressed, and the degradation of indancarbaldehyde can be suppressed. In addition, when the content of the amine is less than 1000 ppm by mass, the precipitation of a solid comprising a benzylamine-boron trifluoride complex in a distillation column tends to be able to be suppressed.

The lower limit of the content of the amine is ideally 0 ppm by mass but may be more than 0 ppm by mass and may be 10 ppm by mass or more.

The content of the amine in indan in this embodiment is preferably 0 ppm by mass or more and less than 1000 ppm by mass, more preferably more than 0 ppm by mass and less than 1000 ppm by mass, and further preferably more than 0 ppm by mass and less than 650 ppm by mass.

As used herein, the above step of obtaining a reaction liquid comprising indancarbaldehyde is also referred to as an indan-formylation reaction step.

[Indan-Formylation Reaction Step]

The formylation reaction of indan is carried out by reacting indan with carbon monoxide in the presence of hydrogen fluoride and boron trifluoride catalysts. Indancarbaldehyde can be obtained in good yield by this production method. In addition, the hydrogen fluoride and the boron trifluoride used as the catalysts have high volatility and therefore can be recovered in a complex decomposition step described later and can be reused. From this, the catalysts used need not be discarded, and the production method is economically excellent, and at the same time the environmental load is also reduced.

The carbon monoxide used in the formylation reaction of indan may contain inert gases such as nitrogen and/or methane, and the partial pressure of carbon monoxide is preferably 0.5 to 5 MPa, more preferably 1 to 3 MPa, in terms of gauge pressure. By setting the partial pressure of carbon monoxide at 0.5 MPa or more, the formylation reaction proceeds sufficiently, and indancarbaldehyde can be obtained in good yield with side reactions such as isomerization and/or polymerization suppressed. Even if the partial pressure of carbon monoxide is higher than 5 MPa, no reaction merit is obtained, and problems such as requiring an apparatus having higher pressure resistance performance are caused.

The amount of hydrogen fluoride used in the formylation reaction of indan is preferably 5.0 mol or more, more preferably 7.0 mol or more, with respect to 1 mol of the raw material indan from the viewpoint of increasing the raw material conversion rate. The upper limit of the amount of hydrogen fluoride is not particularly limited but is usually preferably 30.0 mol or less because the volumetric efficiency of the apparatus decreases, and the amount of hydrogen fluoride that needs to be recovered increases.

The amount of boron trifluoride used in the formylation reaction of indan is preferably 1.0 mol to 3.5 mol, more preferably 1.5 mol to 2.5 mol, with respect to 1 mol of indan. When the amount of boron trifluoride is less than 1.0 mol, the formylation reaction tends to be slow. When the amount of boron trifluoride is more than 3.5 mol, the partial pressure of carbon monoxide in the gas phase tends to decrease to cause a decrease in the yield of indancarbaldehyde.

The formylation reaction of indan is preferably carried out at a temperature in the range of −50° C. or more and 30° C. or less, more preferably −30° C. or more and 20° C. or less, and further preferably −25° C. or more and 0° C. or less. By setting the reaction temperature at 30° C. or less, yield decrease due to the production of polymerization products as by-products can be suppressed. By setting the reaction temperature at −50° C. or more, the formylation reaction can be allowed to proceed sufficiently.

The reaction time of the formylation reaction of indan is preferably 1 to 5 hours with the raw material supply time and the subsequent reaction time combined, from the viewpoint of obtaining a sufficient conversion rate of indan.

The raw material indan in the formylation reaction of indan may be dissolved in a reaction solvent inert to indan, hydrogen fluoride, and boron trifluoride. Examples of such a reaction solvent can include saturated aliphatic hydrocarbons such as hexane, heptane, and decane. By using the reaction solvent, the polymerization reaction is suppressed, and the yield can improve. Whether or not the reaction solvent is used and the amount of the reaction solvent used are appropriately selected because the use of a large amount of the solvent causes a decrease in the volumetric efficiency of the reaction, and the worsening of the specific energy consumption required for separation.

The mode of the formylation reaction of indan in this embodiment is not particularly limited as long as it is a reaction method in which the liquid phase and the gas phase can mix sufficiently. Any method, for example, a batch, semibatch, or continuous method, can be adopted.

The indan in this embodiment is preferably the reaction product of the hydrogenation reaction of a raw material comprising indene.

For the raw material comprising indene to be subjected to the hydrogenation reaction, indene having a purity of 90% by mass or more industrially purified from deoxidized and base-removed coal tar oil by the known technique such as distillation can be used. In other words, the content of indene contained in the above raw material is preferably 90% by mass or more.

In addition, the raw material comprising indene may comprise benzonitrile, and the content of the benzonitrile is preferably 0.5 to 10% by mass. The raw material comprising indene preferably has a low content of components other than benzonitrile. When the content of the benzonitrile is 0.5 to 10% by mass, the content of the amine contained in the indan in this embodiment tends to be able to be reduced.

The content of benzonitrile in the raw material comprising indene is more preferably 0.5 to 5.0% by mass, further preferably 0.5 to 2.5% by mass.

Further, the indan in this embodiment may comprise benzonitrile, and the content of the benzonitrile is preferably 0.5 to 10% by mass. When the content of benzonitrile in the indan is 10% by mass or less, the production efficiency of indancarbaldehyde tends to be excellent. When the content of benzonitrile in the indan is 0.5% by mass or more, indan is easily available.

The content of benzonitrile in the indan is more preferably 0.5 to 5.0% by mass, further preferably 0.5 to 2.5% by mass.

The indancarbaldehyde in this embodiment is not limited as long as it is a compound in which hydrogen on the aromatic ring of an indan group is replaced by one or more aldehyde groups. For example, indan-5-carbaldehyde represented by formula (1) and indan-4-carbaldehyde are preferred, and indan-5-carbaldehyde represented by formula (1) is more preferred.

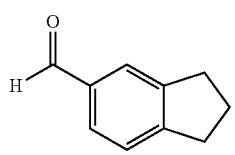

(1)

The amine contained in the indan in this embodiment is preferably one or more selected from the group consisting of benzylamine, dibenzylamine, and tribenzylamine.

[Indene-Reduction Reaction Step]

As described above, the indan in this embodiment can be obtained by subjecting a raw material comprising indene to a hydrogenation reaction.

Therefore, this embodiment may further comprise steps of:

reducing a raw material comprising indene in the presence of a catalyst and hydrogen to obtain a reaction product comprising indan, and distilling and purifying the reaction product comprising indan to obtain indan having a content of an amine of less than 1000 ppm by mass.

In other words, one of preferred modes of this embodiment is a method for producing indancarbaldehyde, comprising steps of:

reducing a raw material comprising indene in the presence of a catalyst and hydrogen to obtain a reaction product comprising indan, and distilling and purifying the reaction product comprising indan to obtain indan having a content of an amine of less than 1000 ppm by mass; and reacting the indan having a content of the amine of less than 1000 ppm by mass with carbon monoxide in the presence of hydrogen fluoride and boron trifluoride to obtain a reaction liquid comprising indancarbaldehyde.

The pressure of hydrogen is not particularly limited but is usually in the range of normal pressure to 2.0 MPa, preferably 1.0 to 2.0 MPa, in terms of gauge pressure. By setting the hydrogen pressure at 1.0 to 2.0 MPa in terms of gauge pressure, the reduction reaction of indene tends to be able to proceed sufficiently, and the production of benzylamine by the reduction reaction of benzonitrile tends to be able to be suppressed.

The reaction temperature of the hydrogenation reaction is preferably at 20° C. to 100° C., and is more preferably 35° C. to 100° C. from the viewpoint of efficiently performing the reduction reaction of indene.

The catalyst used in the above hydrogenation reaction preferably comprises a catalyst comprising palladium and/or platinum. The catalyst compound is usually in the state of a metal but may be in the form of such an oxide as to be easily reduced to a metal under the reaction conditions. These metals may be in the form of being supported on a support.

The amount of the catalyst is preferably 0.01 to 10% by mass, more preferably 0.5 to 5% by mass, with respect to the raw material comprising indene to be subjected to the hydrogenation reaction. When the amount of the catalyst is less than 0.01% by mass, the reaction rate tends to decrease. When the amount of the catalyst is more than 10% by mass, the hydrogenation may proceed excessively to produce by-products.

The hydrogenation reaction can also be performed without a solvent, but, for example, a hydrocarbon, an alcohol, an ether, or a mixture thereof may be used as a solvent.

Examples of the hydrocarbon can include toluene, decane, and hexane.

Examples of the alcohol can include methanol, ethanol, n-propanol, i-propanol, n-butanol, i-butanol, and sec-butanol.

Examples of the ether can include dialkyl ethers such as diethyl ether, dibutyl ether, diisobutyl ether, diamyl ether, diisoamyl ether, methyl butyl ether, methyl isoamyl ether, and ethyl isobutyl ether.

The amount of the solvent when the solvent is used is usually preferably in the range of 0.1 to 30 times, more preferably in the range of 0.2 to 20 times the mass of the reaction substrate.

The reaction time of the hydrogenation reaction is preferably 0.5 to 5 hours because a sufficient conversion rate of indene is obtained.

The mode of the hydrogenation reaction is not particularly limited as long as a catalytic reduction reaction is possible. A usually used known mode can be used. Examples of the mode can include a slurry bed reaction in which a catalyst is fluidized with a fluid for a catalytic reduction reaction, and a fixed bed reaction in which a catalyst is packed and immobilized and a fluid is supplied for a catalytic reduction reaction. The above slurry bed reaction and fixed bed reaction can be performed using a slurry bed reactor and a fixed bed reactor respectively.

Dibenzylamine and tribenzylamine that can be produced from benzonitrile in the reduction reaction of indene described above have a large difference in boiling point from indan and therefore can be easily removed by distillation. The distillation and purification can be performed using a rectifying column.

[Complex Decomposition Step]

The indancarbaldehyde-hydrogen fluoride-boron trifluoride complex solution obtained in the formylation reaction step can be separated into a decomposition aid solution of indancarbaldehyde, which is the product, and hydrogen fluoride and boron trifluoride, catalysts, by being thermally decomposed with a heat medium. The separated hydrogen fluoride and boron trifluoride need not be discarded and can be reused as catalysts in the reaction.

In other words, the production method in this embodiment preferably further comprises a step of adding a heat medium to the reaction liquid comprising indancarbaldehyde followed by heating for separation into a flow comprising hydrogen fluoride and boron trifluoride and a flow comprising indancarbaldehyde and the heat medium. As used herein, the step of separation into a flow comprising hydrogen fluoride and boron trifluoride and a flow comprising indancarbaldehyde and the heat medium is also referred to as a complex decomposition step.

Preferred examples of the above heat medium can include aromatic solvents such as benzene and toluene.

Among the above heat media, benzene is preferred because it is effective in suppressing the degradation of indancarbaldehyde in the complex decomposition step. Benzene may be used alone as the heat medium, and a mixture of benzene and toluene can also be preferably used.

The heating of the reaction liquid comprising indancarbaldehyde is preferably performed under the conditions of the pressure range of 0.1 to 1.0 MPa in terms of gauge pressure and the temperature range of 120 to 180° C. When the temperature is lower than 120° C., the decomposition of the indancarbaldehyde-hydrogen fluoride-boron trifluoride complex tends not to proceed sufficiently. When the temperature is higher than 180° C., the heating is economically disadvantageous because a high temperature heat source is required, and the thermal decomposition of the aldehyde tends to occur easily.

The flow comprising indancarbaldehyde and the heat medium can be further purified by distillation, and the target indancarbaldehyde can be obtained with high purity. As used herein, the flow comprising indancarbaldehyde and the heat medium is also referred to as the heat medium solution of indancarbaldehyde obtained in the complex decomposition step.

The decomposition rate of the indancarbaldehyde-hydrogen fluoride-boron trifluoride complex contained in the heat medium solution of indancarbaldehyde obtained in the complex decomposition step is ideally 100% and preferably 97.0% or more, more preferably 98.0% or more, and further preferably 99.0% or more. As used herein, the indancarbaldehyde-hydrogen fluoride-boron trifluoride complex is also referred to as undecomposed boron trifluoride and/or a boron trifluoride complex.

When the decomposition rate of the boron trifluoride complex is 97.0% or more, the precipitation of a solid comprising undecomposed boron trifluoride in a distillation column tends to be able to be suppressed when the heat medium solution of indancarbaldehyde obtained in the complex decomposition step is further purified by distillation. In addition, by preventing the precipitation of the solid comprising undecomposed boron trifluoride, indancarbaldehyde can be efficiently produced without stopping the indancarbaldehyde production process.

The decomposition rate of the boron trifluoride complex can be obtained from the following formula. The decomposition rate of the boron trifluoride complex can be specifically obtained by a method described in Examples.

Decomposition rate of boron trifluoride complex (%)=100−(the number of moles of boron trifluoride in heat medium/the number of moles of boron trifluoride in formylation reaction liquid)×100

The aldehyde degradation rate in the complex decomposition step is ideally 0% and preferably 3.5% or less, more preferably 2.0% or less, and further preferably 1.0% or less from the viewpoint of obtaining indancarbaldehyde in high yield and reducing the production cost.

The aldehyde degradation rate in the complex decomposition step can be obtained from the following formula. The aldehyde degradation rate can be specifically obtained by a method described in Examples.

Aldehyde degradation rate (%)=100−(the number of moles of indancarbaldehyde in heat medium/the number of moles of indancarbaldehyde in formylation reaction liquid)×100

[Distillation and Purification Step]

The heat medium solution of indancarbaldehyde obtained in the complex decomposition step can be further purified by distillation as described above, and the target indancarbaldehyde can be obtained with high purity by such purification.

In other words, the production method in this embodiment may further comprises a step of distilling and purifying the flow comprising indancarbaldehyde and the heat medium. As used herein, the above distilling and purifying step is also referred to as a distillation and purification step.

Examples of the distilling and purifying step can include a step of washing the above flow comprising indancarbaldehyde and the heat medium with a basic aqueous solution as required, and performing rectification using a rectifying column to obtain indancarbaldehyde as the main fraction.

Examples of the basic aqueous solution can include an aqueous solution having a pH of 7.5 to 12. Specifically, a sodium hydroxide aqueous solution is preferred, and 1 to 10% by mass sodium hydroxide aqueous solution is more preferred.

EXAMPLES

This embodiment will be described in more detail below by Examples, but the present invention is not limited to these Examples.

The compositions in the steps described later were evaluated by preparing calibration curves using gas chromatograph GC-2010 Plus (manufactured by SHIMADZU CORPORATION) and n-decane (reagent grade, manufactured by Wako Pure Chemical Industries, Ltd.) as an internal standard substance. As the capillary column, DB-1 having an inner diameter of 0.32 mm φ and a length of 30 m manufactured by Agilent Technologies was used. In the temperature increase program, the temperature was increased from 60° C. to 280° C. at a rate of 5° C./min and maintained for 30 min.

Methods for preparing indan are shown in the following Experimental Examples 1 to 7.

Experimental Example 1

[Indene-Reduction Reaction Step]

800.2 g of indene comprising 97.2% by mass of indene, 0.5% by mass of indan, 1.6% by mass of benzonitrile, and 0.7% by mass of an alkylbenzene (manufactured by JFE Chemical Corporation), and 16.0 g of a 5% palladium-carbon catalyst (manufactured by N.E. CHEMCAT Corporation, water-containing product, PE type) were charged into a stainless steel autoclave having an internal volume of 5 L which was equipped with a magnetic force induction type stirrer and whose internal temperature could be controlled by a jacket. The mixture was stirred at 70° C. and a hydrogen pressure of 2.0 MPa for 3 hours for a reduction reaction. The reaction liquid was filtered to remove the catalyst to obtain 788.2 g of a reaction liquid comprising 97.7% by mass of indan, 1.1% by mass of benzonitrile, 24 ppm by mass of benzylamine, 0.3% by mass of dibenzylamine, and 0.8% by mass of other components.

[Distillation and Purification Step]

When the obtained reaction liquid was rectified using a rectifying column having a theoretical plate number of 20, 752.3 g of indan comprising 98.1% by mass of indan, 1.1% by mass of benzonitrile, 20 ppm by mass of benzylamine, and 0.8% by mass of the alkylbenzene was obtained at 102 to 104° C./75 torr as the main fraction. The isolated yield of indan was 92.8 mol % with respect to indene.

Experimental Example 2

The reduction reaction and distillation and purification were performed by the same operations as in Experimental Example 1 except that the temperature of the reduction reaction of indene was 100° C. The composition of the obtained indan is shown in Table 2.

Experimental Example 3

The reduction reaction and distillation and purification were performed by the same operations as in Experimental Example 1 except that the temperature of the reduction reaction of indene was 30° C. The composition of the obtained indan is shown in Table 2.

Experimental Example 4

The reduction reaction and distillation and purification were performed by the same operations as Experimental Example 1 except that 16.0 g of a 2% platinum-carbon catalyst (manufactured by N.E. CHEMCAT Corporation, water-containing product) was used, and the reduction reaction was at 100° C. The composition of the obtained indan is shown in Table 2.

Experimental Examples 5 to 7

Reduction and distillation and purification were performed by the same operations as Experimental Example 1 except that a catalyst and reaction conditions shown in Table 1 were used. The composition of the obtained indan is shown in Table 2.

TABLE 1

| | Catalyst type | Amount of catalyst (% by mass) | Temperature (° C.) | Hydrogen pressure (MPa) | Stirring time (hr) |
|---|---|---|---|---|---|
| Experimental Example 1 | 5% palladium/carbon | 2.0 | 70 | 2.0 | 3 |
| Experimental Example 2 | 5% palladium/carbon | 2.0 | 35 | 2.0 | 5 |
| Experimental Example 3 | 5% palladium/carbon | 2.0 | 100 | 2.0 | 2 |
| Experimental Example 4 | 2% platinum/carbon | 2.0 | 100 | 2.0 | 3 |
| Experimental Example 5 | nickel/diatomaceous earth (*1) | 2.0 | 100 | 2.0 | 3 |
| Experimental Example 6 | copper-chromium (*2) | 4.0 | 150 | 2.0 | 10 |
| Experimental Example 7 | 5% ruthenium/carbon (*3) | 2.0 | 100 | 2.0 | 3 |

(*1) nickel/diatomaceous earth catalyst: N103 manufactured by JGC Catalysts and Chemicals Ltd.
(*2) copper-chromium catalyst: N2035D manufactured by JGC Catalysts and Chemicals Ltd.
(*3) 5% ruthenium-carbon catalyst: manufactured by N.E. CHEMCAT Corporation, containing water, B type

TABLE 2

| | | Benzonitrile (% by mass) | Indan (% by mass) | Indene (% by mass) | Alkylbenzene (% by mass) | Benzylamine (ppm by mass) | Dibenzylamine (ppm by mass) | Tribenzylamine (ppm by mass) |
|---|---|---|---|---|---|---|---|---|
| Experimental Example 1 | Before reduction | 1.6 | 0.5 | 97.2 | 0.7 | <10 | <10 | <10 |
| | After reduction | 1.1 | 97.7 | 0.0 | 0.8 | 24 | 3241 | 152 |
| | After distillation | 1.1 | 98.1 | 0.0 | 0.8 | 20 | <10 | <10 |
| Experimental Example 2 | After distillation | 1.5 | 97.8 | 0.0 | 0.7 | <10 | <10 | <10 |
| Experimental Example 3 | After distillation | 0.5 | 98.7 | 0.0 | 0.8 | 53 | <10 | <10 |
| Experimental Example 4 | After distillation | 0.9 | 98.3 | 0.0 | 0.8 | 90 | <10 | <10 |
| Experimental Example 5 | After distillation | 0.1 | 98.1 | 0.0 | 0.8 | 8316 | <10 | <10 |
| Experimental Example 6 | After distillation | 0.1 | 95.9 | 2.8 | 0.9 | 2774 | <10 | <10 |
| Experimental Example 7 | After distillation | 0.1 | 98.5 | 0.0 | 0.8 | 5203 | <10 | <10 |

Example 1

[Indan-Formylation Reaction Step]

An experiment was performed using a stainless steel autoclave having an internal volume of 10 L which was equipped with a magnetic force induction type stirrer, three inlet nozzles in the upper portion, and one drawing nozzle at the bottom and whose internal temperature could be controlled by a jacket. First, the inside of the autoclave was purged with carbon monoxide, then 906 g (45.3 mol) of hydrogen fluoride (manufactured by Morita Chemical Industries Co., Ltd.) and 686.6 g (10.1 mol) of boron trifluoride (manufactured by STELLA CHEMIFA CORPORATION) were charged, and the liquid temperature was set at −20° C. Then, the autoclave was pressurized to 2 MPa with carbon monoxide. While the reaction temperature was maintained at −20° C., and the reaction pressure was kept at 2 MPa, 665 g of the indan obtained in Experimental Example 4 was supplied from the upper portion of the autoclave over 30 min, and stirring was continued for about 30 min until no absorption of carbon monoxide was noted. 5.5 mol of indan was contained in the indan obtained in Experimental Example 4.

[Complex Decomposition Step]

Benzene was supplied at a flow rate of 10 g/min at a pressure of 0.4 MPa and a column bottom temperature of 145° C., and the formylation reaction liquid obtained above was supplied to a complex decomposition column under reflux at a flow rate of 10 g/min. The complex decomposition column was made of SUS316L, had an inner diameter of 760 mm and a length of 1760 mm, and was packed with ½ inch Teflon® Raschig rings. The hydrogen fluoride and the boron trifluoride were recovered from the column top, and a benzene solution comprising about 30% by mass of indan-5-carbaldehyde was drawn from the column bottom. When the content of undecomposed boron trifluoride in the obtained benzene solution was obtained, it was 0.06% by mass. When the boron trifluoride complex decomposition rate was calculated from the following formula, it was 99.7%. When the aldehyde degradation rate in the complex decomposition step was calculated from the following formula, it was 0.8%.

Boron trifluoride complex decomposition rate (%)=100−(the number of moles of boron trifluoride in benzene solution/the number of moles of boron trifluoride in formylation reaction liquid)×100 the aldehyde degradation rate (%)=100−(the number of moles of indan-5-carbaldehyde in the benzene solution/the number of moles of indan-5-carbaldehyde in the formylation reaction liquid)×100

[Distillation and Purification Step]

When the benzene solution obtained above was washed with a 2% by mass sodium hydroxide aqueous solution followed by rectification using a rectifying column having a theoretical plate number of 20, 592 g of indan-5-carbaldehyde was obtained as the main fraction at 131 to 135° C./15 torr. The purity of the indan-5-carbaldehyde was 97.8%, and the indan-5-carbaldehyde isolated yield with respect to indan was 72.0 mol %.

Example 2

0.40 g of benzylamine was added to 665 g of the indan obtained in Experimental Example 1, to obtain indan A comprising 620 ppm by mass of benzylamine. 5.5 mol of indan was contained in the indan obtained in Experimental Example 1.

The formylation reaction step and the complex decomposition step were performed by the same operations as in Example 1 except that the above indan A was used. When the content of undecomposed boron trifluoride in the benzene solution comprising about 30% by mass of indan-5-carbaldehyde obtained from the column bottom was obtained, it was 0.10% by mass. When the boron trifluoride complex decomposition rate was calculated, it was 99.5%. The aldehyde degradation rate in the complex decomposition step was 0.9%.

Comparative Example 1

The formylation reaction step and the complex decomposition step were performed by the same operations as in Example 1 except that the indan obtained in Experimental Example 5 was used. When the content of undecomposed boron trifluoride in the benzene solution comprising about 30% by mass of indan-5-carbaldehyde obtained from the column bottom was obtained, it was 0.79% by mass. When the boron trifluoride complex decomposition rate was calculated, it was 96.1%.

The aldehyde degradation rate in the complex decomposition step was 4.0%. When indan comprising benzylamine is used, the boron trifluoride complex decomposition rate worsens, and an increase in the degradation rate of indan-5-carbaldehyde, and an increase in production cost due to the loss of boron trifluoride are caused, which are disadvantageous in the production of indan-5-carbaldehyde.

Comparative Example 2

1.0 g of benzylamine was added to 665 g of the indan obtained in Experimental Example 2, to obtain indan B comprising 1535 ppm by mass of benzylamine. 5.5 mol of indan was contained in the indan obtained in Experimental Example 2.

The formylation reaction step and the complex decomposition step were performed by the same operations as in Example 1 except that the above indan B was used. When the content of undecomposed boron trifluoride in the benzene solution comprising about 30% by mass of indan-5-carbaldehyde obtained from the column bottom was obtained, it was 0.25% by mass. When the boron trifluoride complex decomposition rate was calculated, it was 98.7%. The aldehyde degradation rate in the complex decomposition step was 1.6%.

The results of Examples 1 to 2 and Comparative Examples 1 to 2 are shown in Table 3.

Whether solids precipitated or not was evaluated by carrying out the same distillation and purification step as Experimental Example 1 and visually observing the precipitation of solids in the condenser portion.

TABLE 3

| | Example 1 | Example 2 | Comparative Example 1 | Comparative Example 2 |
|---|---|---|---|---|
| Indan subjected to formylation reaction step and complex decomposition step | Indan obtained in Experimental Example 4 | Indan obtained in Experimental Example 1 | Indan obtained in Experimental Example 5 | Indan obtained in Experimental Example 2 |
| Amount of benzylamine added (g) | — | 0.40 | — | 1.0 |
| Amines in indan (ppm by mass) | <110 | <640 | <8336 | <1555 |
| Undecomposed boron trifluoride (% by mass) | 0.06 | 0.10 | 0.79 | 0.25 |
| Boron trifluoride complex decomposition rate (%) | 99.7 | 99.5 | 96.1 | 98.7 |
| Aldehyde degradation rate (%) | 0.8 | 0.9 | 4.0 | 1.6 |
| Whether solids precipitated or not | Solids did not precipitate | Solids did not precipitate | Solids precipitated | Small amount of solids precipitated |

This application is based on Japanese Patent Application No. 2017-082178 filed on Apr. 18, 2017, the contents of which are incorporated herein by reference.

INDUSTRIAL APPLICABILITY

Indancarbaldehyde obtained by the production method of the present invention has the industrial applicability of being useful as a raw material for the production of various industrial chemical raw materials, perfumes, medicines, agricultural chemicals, optical functional materials, electronic functional materials, and the like.

The invention claimed is:

1. A method for producing indancarbaldehyde, comprising:
   reacting indan with carbon monoxide in the presence of hydrogen fluoride and boron trifluoride to obtain a reaction liquid comprising indancarbaldehyde, wherein the indan comprises an amine, and a content of the amine is less than 1000 ppm by mass.

2. The method for producing indancarbaldehyde according to claim 1, wherein the indan is a reaction product of a hydrogenation reaction of a raw material comprising indene.

3. The method for producing indancarbaldehyde according to claim 2, wherein a content of the indene contained in the raw material is 90% by mass or more.

4. The method for producing indancarbaldehyde according to claim 2, wherein the raw material comprising the indene comprises benzonitrile, and
   a content of the benzonitrile is 0.5 to 10% by mass.

5. The method for producing indancarbaldehyde according to claim 1, wherein the indan comprises benzonitrile, and
   a content of the benzonitrile is 0.5 to 10% by mass.

6. The method for producing indancarbaldehyde according to claim 1, wherein the indancarbaldehyde is indan-5-carbaldehyde represented by formula (1):

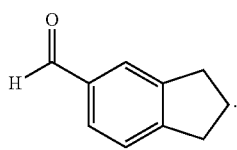

(1)

7. The method for producing indancarbaldehyde according to claim 1, wherein the amine contained in the indan is at least one selected from the group consisting of benzylamine, dibenzylamine, and tribenzylamine.

8. The method for producing indancarbaldehyde according to claim 1, further comprising:
   adding a heat medium to the reaction liquid comprising the indancarbaldehyde followed by heating for separation into a flow comprising the hydrogen fluoride and the boron trifluoride and a flow comprising the indancarbaldehyde and the heat medium.

9. The method for producing indancarbaldehyde according to claim 8, wherein the heating is performed under conditions of a temperature of 120 to 180° C. and 0.1 to 1.0 MPa in terms of gauge pressure.

10. The method for producing indancarbaldehyde according to claim 1, further comprising:
    reducing a raw material comprising indene in the presence of a catalyst and hydrogen to obtain a reaction product comprising indan, and
    distilling and purifying the reaction product comprising the indan to obtain indan having a content of an amine of less than 1000 ppm by mass.

11. The method for producing indancarbaldehyde according to claim 10, wherein the reduction is performed under conditions of a temperature of 20 to 100° C. and normal pressure to 2.0 MPa in terms of gauge pressure.

12. The method for producing indancarbaldehyde according to claim 10, wherein the catalyst comprises palladium and/or platinum.

* * * * *